Figure 1:
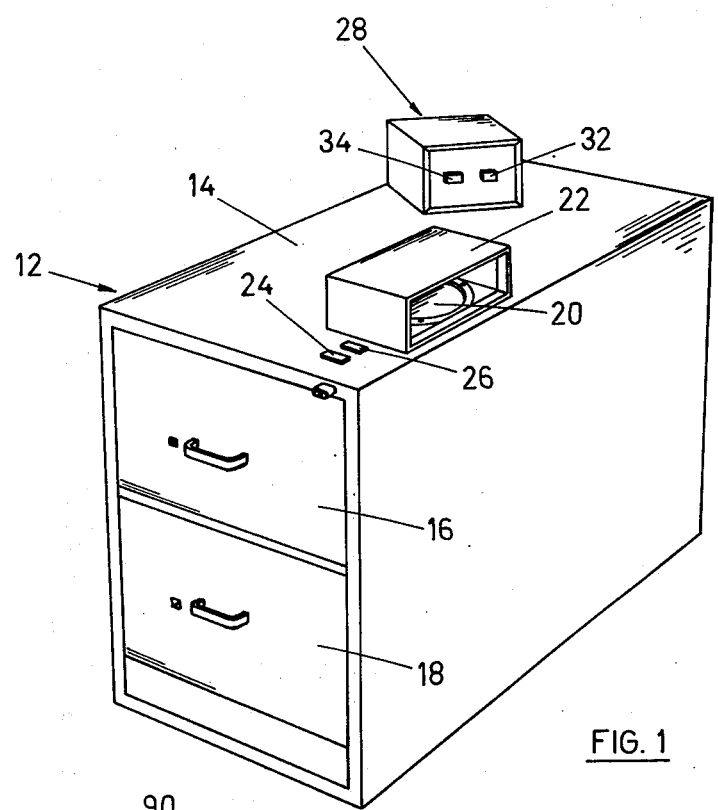

United States Patent [19]

Biederman

[11] 4,022,054
[45] May 10, 1977

[54] METHOD AND APPARATUS FOR USE IN DETECTING FAINT OLFACTORY STIMULI

[76] Inventor: Gerald Bernard Biederman, 113 Argonne Crescent, Willowdale, Ontario, Canada

[22] Filed: Sept. 30, 1975

[21] Appl. No.: 618,046

[52] U.S. Cl. .............................. 73/23; 116/114 N; 119/1
[51] Int. Cl.[2] ........................................ G01D 21/00
[58] Field of Search .................. 73/23; 340/237 R; 119/29, 1; 116/114 N, 114 P, 72, 1

[56] References Cited

UNITED STATES PATENTS

| 562,731 | 6/1896 | Kraus | 340/237 R |
| 1,027,823 | 5/1912 | Davis | 73/23 |
| 3,693,590 | 9/1972 | Bowers | 119/1 |
| 3,703,101 | 11/1972 | Pence | 73/432 R |

Primary Examiner—James J. Gill

[57] ABSTRACT

An animal cage and means for passing an air current therethrough at a rate which will permit such air to be sampled by an animal in the cage which is sensitized to detect specific scents of relatively low concentration entrained in the air and is also conditioned to respond observably thereto.

13 Claims, 4 Drawing Figures

METHOD AND APPARATUS FOR USE IN DETECTING FAINT OLFACTORY STIMULI

The present invention relates to method and apparatus for the rapid detection of faint odors by means of animals which are sensitized to such odors and trained to react thereto.

The use of animals in the detection of odors is not new. For example, use has been reported of dogs specially trained to "sniff out" contraband, loosely describable as narcotics, explosives and so forth and, conceivably, dogs or other animals may be trained to recognize and react to other odors. Generally speaking, however, odors have hitherto had to be relatively strong to be recognized by dogs and, in any event, the time taken for recognition has been disregarded.

Conversely what the invention seeks to accomplish as its main object, is to provide method and apparatus as aforesaid whereby positive odor detection is achievable upon only a brief exposure to the source of the odor which, in fact, need not be concentrated to serve the purposes of the invention. Because of this capability, it becomes possible to use "odor-screening" effectively in many situations in which it was hitherto quite ineffective or unavailable.

As one example of a situation of this nature, reference may be had to the well-known and comparatively recent problems of "high-jacking" encountered by airlines. To meet this situation, it has become the practice to screen human beings passing through security check points; it being understood that, in most instances, it was not only desirable but essential that the screening be performed unobtrusively and in the briefest of periods to avoid offending the passengers on the one hand and, as well, to avoid delaying the traffic on the other hand.

This type of situation is very familiar in air travel and the description of the invention in relation thereto is intended only for the illustrative purposes of this submission and is not by any means intended to be construed as a full catalogue of the areas capable of being served by the invention.

In this respect, the invention is applied to a method and apparatus for sensing stress in human beings.

It is now well known that commercial airlines are required to take elaborate precautions to reduce the likelihood of their aircraft being highjacked. In many countries, especially Canada and the United States, airline passengers are invariably checked for concealed weapons before boarding an aircraft, both the passengers themselves and their hand baggage having to be subjected to metal detector tests. Such examination of every passenger results in several problems, for example invasion of passenger privacy, the high cost of staffing the operation and flight delays. Further, such examinations do not usually result in the location of non-obvious or non-metallic weapons which might be used in a highjacking attempt.

Research has been carried out in an attempt to assess the type of person most likely to make a highjacking attempt, and as a result of this research airport personnel can be trained to watch for particular personality types. However, this is a subjective test which can result in suspicion falling on an innocent person or not falling on a potential highjacker whose appearance does not fit the predetermined personality profile.

It would therefore be extremely valuable, not only to airport security personnel but also in other fields, if some method and apparatus could be provided for recognizing when a person is behaving in an abnormal manner. It is a reasonable presumption that such persons will be under stress, and will exhibit symptoms of stress in some way. Obvious symptoms of stress such as sweating or behaving in a generally nervous manner can be fairly readily recognized, and officials such as custom officials whose work is assisted by recognition of such symptoms are frequently astute in sensing when someone has something to hide. However, many people do not exhibit readily recognizable symptoms when they are under stress caused by the expectation of carrying out an illegal act, but nevertheless do exhibit some symptoms.

It is generally believed by many people that some animals can sense when a person is afraid of them, and this may be by observation of their movements and/or the sensing of a particular scent emitted by a person who is afraid of the animal. It is known that stress in a human produces an increase in epinephrine (adrenalin) in the human system, and that there is a connection between such symptoms and sweat.

According to the present invention, it has been found that the increase in system adrenalin produced by stress can cause the emission of scent from the human body which can be sensed by an animal trained to do so. Also, in accordance with the present invention, it has been found that a rodent such as a gerbil can be trained to detect an adrenalin scent. Applicant has also conducted experiments with a German shepherd dog, and it was found that this animal was capable of being trained to detect an adrenalin scent, although such large animals are not particularly suitable for use with airline passengers, many of whom may become apprehensive merely upon seeing the dog. It is clearly necessary for the person being tested not to be fearful of the test itself.

The present invention therefore provides a method of sensing stress in a human including causing scent from a human to pass into a chamber containing an animal trained to respond to the presence or otherwise of a predetermined concentration of adrenalin in the human scent by actuating a first indicator if said predetermined concentration is present and a second indicator if it is not. Preferably, the animal is a small animal, such as a rodent. The animal in the chamber may be completely concealed from the person being tested, and the testing apparatus may be contained in a housing of reasonable size which appears to be perfectly innocuous to the person being tested.

According to a preferred feature of the invention, a mild electric shock is applied to the animal, while the human scent is passed into the chamber, until the animal actuates one of the indicators. The chamber may have an electrically conductive floor, with the electric shock being applied to the animal therethrough.

First and second movable actuators may be located in the chamber and associated with the first and second indicators respectively, the first actuator being movable by the animal upon sensing the predetermined concentration of adrenalin, and the second actuator being movable by the animal when the predetermined concentration of adrenalin is not sensed.

The responsiveness of the animal may be checked by passing into the chamber a scent from a source containing a predetermined concentration of adrenalin, ascertaining which indicator is actuated by the animal, passing into the chamber a scent from a source containing substantially no adrenalin, and again ascertaining which indicator is actuated by the animal. Each source may include an atomizer, and the scent or "no" scent from the respective source may be passed into the chamber by a supply of compressed air associated with the atomizers.

Human scent may be passed into the chamber through a conduit extending from a human scent-receiving aperture to the chamber, with a fan being operable to pass air along the conduit from the scent-receiving aperture to the chamber.

There may be means responsive to the presence of a human positioned to pass human scent into the chamber, with the responsive means operating to cause the electrical shock to be applied to the animal in the chamber when a human is positioned as aforesaid. Such responsive means may comprise a photoelectric cell.

As mentioned above, the animal is preferably a rodent. It has been found that gerbils, especially Mongolian gerbils, are particularly suitable for training in accordance with the invention.

Figure 4:
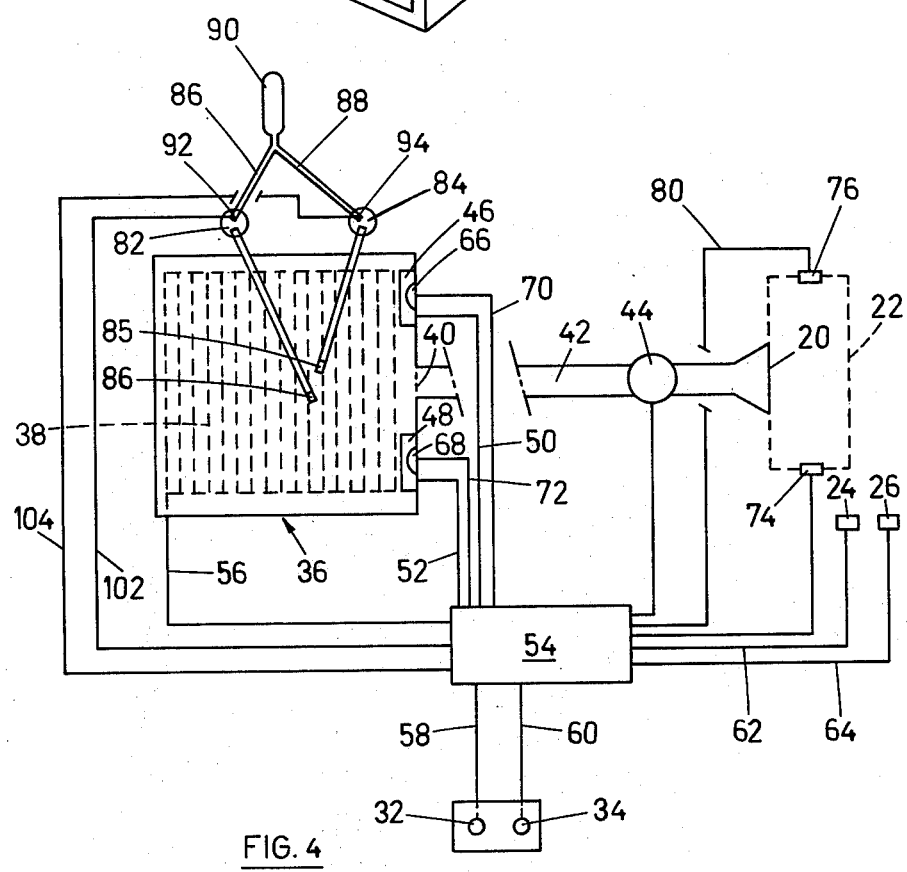
Figure 2:
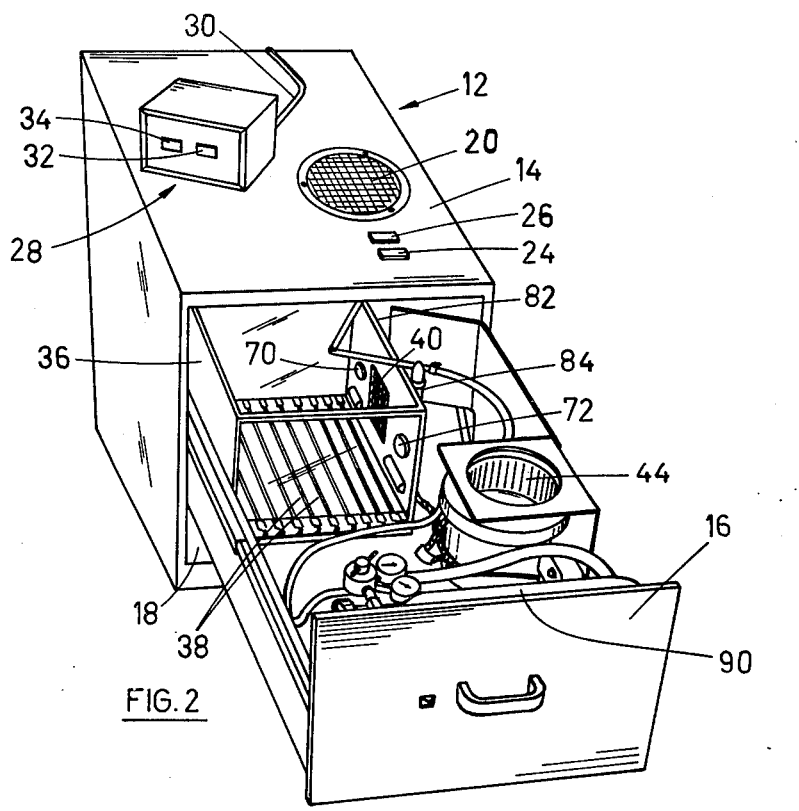
Figure 3:
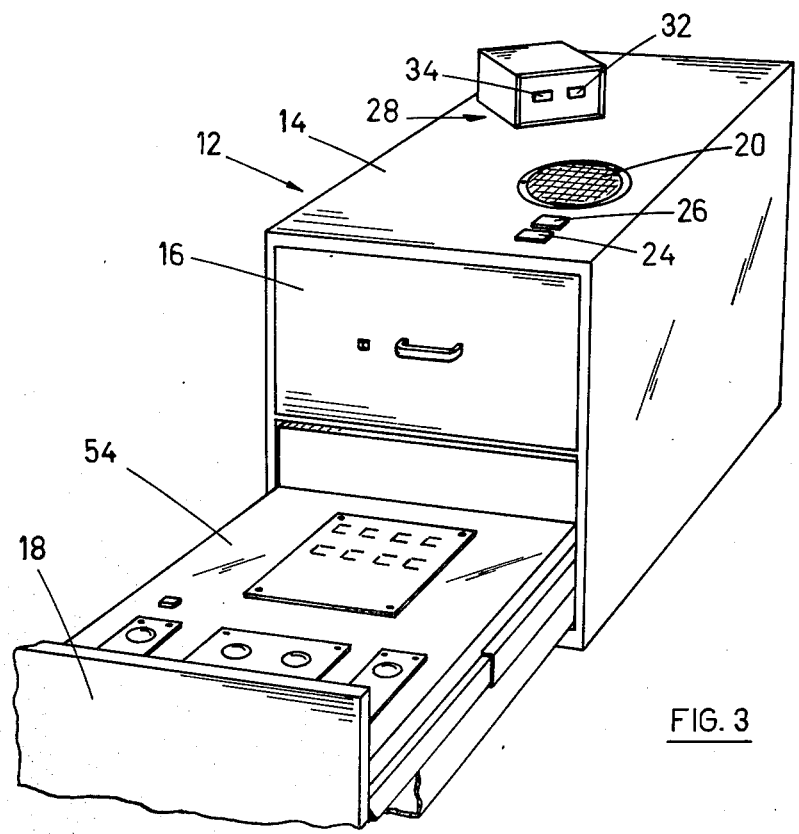

One embodiment of the present invention will now be described, by way of example, with reference to the accompanying drawings, of which:

FIG. 1 is a perspective view of stress sensing apparatus illustrating in particular its innocuous appearance, FIG. 2 is a perspective view of the stress sensing apparatus of FIG. 1 with the upper drawer open to illustrate the animal chamber and associated equipment, FIG. 3 is a similar view but showing the lower drawer opened to illustrate the electrical controls of the apparatus, and FIG. 4 is a block diagram showing various parts of the stress sensing apparatus.

Referring to the drawings, stress sensing apparatus suitable for use in an airport security system comprises a cabinet 12 having a housing 14 and upper and lower drawers 16, 18 respectively. The cabinet 12 is in fact a somewhat modified standard two drawer filing cabinet of the kind with which most people are familiar. The top of the housing 14 has a scent-receiving aperture 20 partially covered by a cover 22 as shown in FIG. 1 (but omitted in FIGS. 2 and 3), into which a person can place a hand so as to position the hand adjacent the scent-receiving aperture 20. Adjacent the scent-receiving aperture 20, but outside the cover 22, are two lights, namely a red light 24 and a green light 26. As will be described in more detail later, illumination of the red light 24 indicates that the apparatus is ready to carry out the test, whereupon a hand can be positioned within the cover 22, and the illumination of the green light 26 indicates to the person being tested that the test has been completed.

A stress indicator box 28, shown in FIGS. 1 to 3 positioned on top of the cabinet 12, is connected by an electrical cable 30 to the electrical circuit in the lower drawer 18, as will also be described later, and is provided with red and green lights 32, 34 respectively. The stress indicator box 28 may be positioned so that its indicator lights 32, 34 can only be seen by the operator of the apparatus and not by the person being tested.

Illumination of the red light 32 will indicate the sensing of stress in the person being tested, and illumination of the green light 34 will indicate that no stress has been sensed in the person being tested.

It will thus be readily observed that the stress sensing apparatus is not likely of itself to cause anxiety in the person being tested, since it looks very much like a familiar piece of office equipment.

The top drawer 16 contains an animal chamber 36 of a suitable size to accommodate a Mongolian gerbil. The floor of the chamber has parallel metal bars 38 through which an electrical current can be passed to apply an electric shock to the animal through its feet. An air inlet 40 is centrally located in one wall of the chamber 36, and is connected by a conduit 42 to the outlet of a fan 44, whose inlet is positioned under the scent-receiving aperture 20 in the top of the cabinet 12.

A pair of actuators in the form of levers 46, 48 are pivotally mounted on the inner wall of the chamber 36 on opposite sides of the air inlet 40, and are positioned just above the floor, so that each lever 46, 48 can be pressed down by the front feet of the gerbil. Each lever 46, 48 is resiliently biased to an upper or "off" position by a spring (not shown). The levers 46, 48 which are actually electrical switches, are connected by electric leads 50, 52 respectively to a control box 54, which is located in the lower drawer 18.

The electric control box 54 is connected by lead 56 to the electric floor bars 38 in the chamber 36, by leads 58, 60 to the red and green lights 32, 34 respectively in the indicator box 28, and by leads 62, 64 to the red and green lights 24, 26 respectively in the top of the cabinet 12.

Actuator or stimulus lights 66, 68 are mounted in the chamber 36 above each actuator lever, 46, 48 respectively, and are connected by leads 70, 72 to the control box 54.

As indicated in FIG. 4, although they are not shown in FIGS. 1 to 3, a photocell 74 is mounted within the cover 22 opposite a light 76, so that when a hand is inserted into the cover 22 the aperture 20, the hand interupts the beam of light from the light 76 to the photocell 74. The photocell 74 and light 76 are connected to the control box 54 by leads 78, 80 respectively.

The upper drawer 16 also contains a pair of atomizers 82, 84 having inlets connected by conduits 86, 88 respectively to a compressed air supply 90, the conduits 86, 88 being fitted with electromagnetically operated valves 92, 94 respectively. The outlets nozzles 83, 85 from the atomizers 82, 84 respectively are positioned over the chamber 36, and the electromagnetic valves 92, 94 are connected to the control box 54 by leads 102, 104 respectively.

The nature of the elecrical circuitry within the control box 54, which will of course be connected to a source of power in use, will be readily apparent to the man skilled in the art from the following description of the operation of the apparatus, and hence it is not necessary to actually describe this circuitry in detail.

In use of the apparatus, the atomizer 82 contains sodium chloride solution, and the atomizer 84 contains sodium chloride solution plus a suitable concentration of adrenalin, for example one part adrenalin to one thousand parts sodium chloride. Initially, to train the animal in the chamber 36, the control box 54 is set by means of relevant controls shown in FIG. 3, to cause a mild electric shock, for example of the order of 0.8mA, to be applied to the animal through the foot bars 38. The control box 54 is also set so that the animal can terminate the electrical shock by placing its front feet on and consequently depressing the actuator levers 46 or 48. Such application of electric shock is repeated many times until the animal is responding rapidly.

The animal is then trained to sense presence or absence of adrenalin. First, with the applied electric shock, either adrenalin bearing air from the atomizer 84 is supplied to the chamber 36 through nozzle 85 or no air is supplied, and the control box 54 is set so that the electric shock is terminated only if the actuator lever 46 is depressed by the animal if adrenalin bearing air is supplied, or if actuator lever 48 is depressed by the animal if no air is supplied. Gradually, instead of no air as an alternative to the adrenalin bearing air, air is supplied gradually increasing amounts to the chamber 36 from the atomizer 82 through nozzle 83, until the animal reacts correctly when equal quantities of adrenalin or non-adrenalin bearing air are supplied with the application of the electric shock. To achieve this, the electrically operated valve 92 is adjustable to vary the amounts of air supplied to the atomizer 82 when the valve 92 is opened by a signal along lead 102 from the control box 54.

It has been found by experiment that Mongolian gerbils trained in this way can readily become relatively errorless in the sensing whether adrenalin bearing air or non-adrenalin bearing air is supplied to the chamber.

In practical use, the switching of a master switch prepares the appropriate circuitry in the control box 54, and causes illumination of the red light 24 adjacent the cover 22 on top of the cabinet 12. The hand of a person to be tested is then inserted into the cover 22 so as to interrupt the beam of light to the photocell 74. This initiates a testing sequence. The two actuators or stimulus lights 66, 68 are switched on in the chamber, the fan 44 is switched on to transmit air from the aperture 20 under the cover 22 to the aperture 40 in the chamber 36, and an electric shock is applied shortly thereafter to the animal through the floor bars 38 in the chamber 36. If the air being supplied to the chamber 36 contains more than the predetermined amount of adrenalin, the animal will depress actuator lever 46 to terminate the electric shock, with consequent illumination of red light 32 in the indicator box 28. If the air being supplied contains less than the predetermined concentration of adrenalin, the animal will depress actuator lever 48 to terminate the electric shock, with consequent illumination of the white light 34 in the indicator box 28. Termination of the electric shock also causes red light 24 to go off, and white light 26 to go on adjacent the cover 22.

Thus, the person being tested merely sees the red light 24 go off and white light 26 go on when the test is finished, and cannot see whether the red light 32 or white light 34 was illuminated in the indicator box 28 to indicate to the operator whether or not the air blown into the chamber 36 had above or below the predetermined concentration of adrenalin.

When the person being tested sees white light 26, he can withdraw his hand, with the result that the beam from the light 76 once again actuates the photocell 74, and this causes actuation of the control box 54 to reset the various features described in readiness for the next test.

If necessary, of course, the accuracy of the animal in sensing between adrenalin scents and "no" adrenalin scents can be tested from time to time in the manner previously described using the atomizers 82, 84.

In experiments carried out, Mongolian gerbils have been found to be capable of detecting minute quantities of adrenalin of the order of 500,000: 1 sodium chloride to adrenalin in the relevant atomizer. In an experiment where the animals were tested only at a 1,000 to 1 concentration, the accuracy of each gerbil was tested before and after an actual experimental run during which various people were tested for stress. The people tested were those waiting to board an aircraft, and the gerbils indicated that a small but significant number of people were in a stressed condition. In other words, the scent from their hands contained an adrenalin concentration equal to or above the concentration at which the gerbils were trained. The tests conducted before and after the experimental run indicated that the gerbils were relatively errorless in that there were no more than two errors in twenty trials. In testing the people, the processing time of each person was of the order of one second from the time the photocell 74 initiated the test until the gerbil responded by depressing one of the actuator levers.

The potential of the present invention can now readily be realized. The apparatus described is inconspicuous, so far as the operative parts are concerned, reliable, economical, easily operated, acceptable in terms of time required, acceptable in that the animal "content" is not visible, and reliable in that a facility for testing the animal is built into the apparatus. The use of such a small animal as rodents, and in particular gerbils, in detecting stress in humans by sensing a predetermined concentration of adrenalin has thus been found by the applicant to be of significant potential. It will be found that some gerbils are better for this purpose than others, but unsatisfactory ones can be eliminated by testing.

It will be appreciated the use of the invention in the situation described is not, in itself, exhaustive of the potentialities of the invention; it being obvious that many other situations might well produce premonitory stress in human beings whose early detection could conceivably conduce to the frustration of criminal acts.

Indeed the invention is also applicable to many situations in which stress is not necessarily a factor. For example, it has been found that these animals can also detect the scent of narcotics and explosives placed near the scent-receiving aperture 20. For this purpose, the apparatus may be modified by replacing the photocell 74 by a manually operated switch to initiate a sensing operation. Further, the apparatus may be constructed so as to be readily portable for inspecting places such as baggage compartments. Likewise, portability would enable the apparatus to be carried to the individual instead of waiting for the individual to approach a check point. The equipment, including the atomizers, for checking the responsiveness of the animal may be constructed as a separate unit, so that the output of the atomizers can be placed near the scent-receiving aperture when the animal is to be checked. Also, the cage may be readily detachable from the remainder of the apparatus so that one animal may be easily replaced by another.

Experiments have shown that these animals can detect the scent of the following explosives:

TNT; DNT; RDX; Forcite: Deta sheet; C4; EDGN; PETN 72%, NG 6%; PETN 100%; with or without labelling compounds $SF_6$; CBr $F_2$. The formulae and letters quoted are those by which the explosives and labelling compounds concerned are identified by those skilled in the use of explosives.

Similar experiments have also shown that these animals can detect narcotic drugs such as heroin, cocaine, marijuana and hashish, both in illicit and chemically pure forms.

In each case mentioned above, less than one gram of the substance in question has been detected by the animal by merely exposing the substance to the scent-receiving aperture of the apparatus.

Modifications to the described embodiment, within the scope of the invention, will be readily apparent to the person skilled in the art, the scope of the invention being defined in the appended claims.

What I claim is:

1. Apparatus for use in detecting presence or absence of a scent, comprising a cage harbouring an animal sensitized to recognize said scent in relatively low concentration; means for passing an air current through the cage at a rate which will permit sampling of the air current by the animal and recognition by the animal of said scent at or above said concentration entrained in the air current, and signal means in the cage operable by the animal in response to detection of said scent in said air current; said animal being trained to operate said signal means in response to the detection of said scent in said air current.

2. Apparatus according to claim 1 including means for collecting and passing human scent through the cage and a plurality of signal means selectively operable by said animal according to the presence or absence of said scent in the air current at said concentration.

3. Apparatus according to claim 1 including means for generating and applying an irritant force to the animal while the air current is being passed through the cage and means operable by said animal in conjunction with said signal means for discontinuing generation of said irritant force.

4. Apparatus according to claim 2 including means for applying a mild electric shock to the animal while the air current is being passed through the cage until the animal operates one of said signal means.

5. Apparatus according to claim 2 including a scent source containing a predetermined concentration of a specific scent; another source free of said specific scent, and means for filtering and passing air through and from the respective sources alternately through the cage.

6. Apparatus according to claim 2 wherein said signal means includes movable actuators located in the cage and respectively associated with indicators; each said actuator being movable by the animal to operate an indicator.

7. Apparatus according to claim 4 wherein the cage has an electrically conductive floor, and the electric shock is applied to the animal therethrough.

8. Apparatus according to claim 5 wherein each said scent source includes an atomizer and said means for passing air from the said source into the cage includes a supply of compressed air associated with the atomizers.

9. Apparatus according to claim 5 wherein the means for passing the air current through the cage includes a conduit extending between a scent-receiving aperture and said cage and a fan operable to pass air through the conduit from the scent-receiving aperture into the cage.

10. A method of detecting a faint scent in an air current including passing said air current through a cage containing an animal sensitized to recognize said scent in relatively low concentration and trained to operate signal means in response thereto; said air current being passed through the cage at a rate to permit sampling of the air current by the animal and recognition by the animal of said scent at or above said concentration entrained in the air current.

11. A method according to claim 10 wherein said animal is conditioned to respond to the presence or otherwise of a predetermined concentration of said scent in said air current by actuating one signal means if said predetermined concentration is present therein and another signal means if it is not present.

12. A method according to the claim 11 including applying a mild electric shock to the animal while said air current is passed through the cage until the animal actuates one of the said signal means.

13. A method according to claim 10 including checking the responsiveness of the animal to said scent by passing through the cage an air current containing a predetermined concentration of said scent from one source and ascertaining which signal means is actuated by the animal in response thereto and of passing another air current from another source which is free of said scent in said predetermined concentration and again ascertaining which signal means is actuated by the animal in response thereto.

* * * * *